US005435282A

United States Patent [19]

Haber et al.

[11] Patent Number: 5,435,282
[45] Date of Patent: Jul. 25, 1995

[54] NEBULIZER

[75] Inventors: Terry M. Haber, El Toro; William H. Smedley, Lake Elsinore; Clark B. Foster, Laguna Niguel, all of Calif.

[73] Assignee: Habley Medical Technology Corporation, Laguna Hills, Calif.

[21] Appl. No.: 245,876

[22] Filed: May 19, 1994

[51] Int. Cl.[6] .................... B05B 17/06

[52] U.S. Cl. .................... 128/200.16; 128/200.14; 128/203.12; 128/203.15; 239/338; 261/DIG. 48

[58] Field of Search .................... 128/200.13, 200.16, 128/200.14, 200.15, 200.17, 200.18, 203.12, 203.15, 203.19; 239/338, 102.2; 261/DIG. 48

[56] References Cited

U.S. PATENT DOCUMENTS

| | | | |
|---|---|---|---|
| 482,083 | 9/1892 | Durham | 128/203.19 |
| 4,094,317 | 6/1978 | Wasnich | 128/200.16 |
| 4,294,407 | 10/1981 | Reichl et al. | 128/200.16 |
| 4,300,546 | 11/1981 | Kruber | 128/200.16 |
| 4,301,093 | 11/1981 | Eck | 128/200.16 |
| 4,657,007 | 4/1987 | Carlin et al. | 128/200.18 |
| 4,746,067 | 5/1988 | Svoboda | 128/200.18 |
| 4,790,479 | 12/1988 | Matsumoto | 128/200.16 |
| 4,941,618 | 7/1990 | Hildebrand et al. | 128/200.14 |
| 4,976,259 | 12/1990 | Higson et al. | 128/200.16 |
| 5,060,643 | 10/1991 | Rich et al. | 128/200.23 |
| 5,134,993 | 8/1992 | van der Linden et al. | 128/200.16 |
| 5,152,456 | 6/1992 | Ross et al. | 128/200.16 |
| 5,209,225 | 5/1993 | Glenn | 128/200.18 |
| 5,261,601 | 11/1993 | Ross et al. | 128/200.16 |
| 5,297,542 | 3/1994 | Bacon | 128/200.23 |
| 5,331,954 | 7/1994 | Rex et al. | 128/200.14 |

FOREIGN PATENT DOCUMENTS

| | | | |
|---|---|---|---|
| 186280 | 2/1986 | European Pat. Off. | 128/200.14 |
| 516565 | 12/1992 | European Pat. Off. | 239/102.2 |

*Primary Examiner*—Edgar S. Burr
*Assistant Examiner*—William J. Deane, Jr.
*Attorney, Agent, or Firm*—Hawes & Fischer

[57] ABSTRACT

A hand-held inhalation responsive nebuliser by which a nebulised air stream is created for quick and efficient delivery of a fluid medication to the respiratory tract of a patient through the deep lung. The nebuliser includes a normally open electrical switch and a rotatable trigger ring extending laterally across an air flow path through which a supply of non-medicated ambient air is drawn during inhalation by the patient. The ambient air supply drawn through the nebuliser causes the trigger ring to rotate into contact with and close the electrical switch, whereby a piezoelectric disk is energized to vibrate an emitter mesh. A metered volume of fluid medication delivered to the emitter mesh from a pre-filled medication cartridge is accelerated and pulled through the mesh as a fine mist of fluid droplets to form a nebulised medication plume. The nebulised medication plume is mixed in the mouthpiece of the nebuliser with the supply of non-medicated ambient air to create the nebulised air stream.

20 Claims, 6 Drawing Sheets

NEBULIZER

BACKGROUND OF THE INVENTION

1. Field of the Invention

This invention relates to an improved hand-held nebuliser by which patient inhalation causes a fine mist of fluid medication to be generated and mixed with a non-medicated ambient air supply so that the medication within the resultant composite nebulised air stream can be quickly and efficiently delivered to the respiratory tract of the patient through the deep lung.

2. Background Art

Breath inhalers are generally known by which ambient air inhaled by a patient through a mouthpiece can be mixed with particulate medication so that the medication can be quickly delivered into the blood stream of the patient without the use and accompanying inconvenience of a syringe. In the case of a nebuliser, fluid medication is commonly deposited on the back of a membrane. The membrane is then vibrated at a very high frequency to cause a jet effect which pulls the medication, in the form of a fine mist of droplets, through holes in the membrane.

However, it has been found that if the nebuliser is tilted or if the patient's head is not pulled back far enough, the fluid medication will run (under the influence of gravity) off the membrane. Similarly, if the patient is bedridden or if a complex air path must be established through the nebuliser, little medication will be nebulised to reach the bloodstream of the patient.

Accordingly, it would be preferable to have available an improved inhalation sensitive nebuliser, the use of which is independent of its alignment with in the patient's head so as to maximize the percentage of medication which reaches the deep lung of the patient. It would also be preferable that the improved nebuliser accept a standard, disposable fluid medication cartridge containing a liquid pharmaceutical. In this regard, it is desirable that the patient be able to dispense a precisely metered dose of fluid medication from the cartridge to the membrane so that a nebulised medication plume can be generated and mixed with a non-medicated stream of ambient air in synchronization with the inhalation of the patient.

Reference may be made to U.S. Pat. No. 5,152,456 issued Oct. 6, 1992 which provides one example of a nebuliser device.

SUMMARY OF THE INVENTION

A hand-held inhalation responsive nebuliser is disclosed having a mouth piece removably attached to the distal end of a tubular housing. Pairs of electrically conductive upper and lower holding posts support an electrically conductive emitter plate at the interior of the housing. The emitter plate has an opening therein, and an emitter mesh is seated on the emitter plate to cover the opening. A piezoelectric disk is bonded to the emitter plate at one side of the emitter mesh. Located proximally of the emitter mesh is a fluid deliver valve having a hemispherical membrane surrounded by a fluid collection chamber. The membrane includes a plurality of fluid metering orifices which are normally closed against an electrically conductive needle cannula support (i.e. antenna). The cannula support retains a longitudinally extending needle cannula so that the proximal end of the cannula penetrates the septum of a conventional pre-filled medication cartridge in which a fluid pharmaceutical is stored, and the distal end of the cannula lies within the hemispherical membrane of the fluid delivery valve.

Extending laterally across the tubular housing of the nebuliser is a trigger ring. The trigger ring is rotatable within the air flow path of the housing to control the operation of an electrical switch consisting of a pair of normally open electrical contacts. Located at the proximal end of the nubuliser housing is a rotatable dose selection control knob. The dose selection control knob is rotated around the medication cartridge and advanced distally through the nebuliser housing. An axial (i.e. distal) relocation of the dose selection control knob through the nebulizer housing causes a corresponding axial relocation of a piston through the medication cartridge whereby a metered supply of fluid medication is forced into and expulsed from the needle cannula so as to generate sufficient pressure to distend the hemispherical membrane of the fluid delivery valve and thereby open the fluid metering orifices therethrough. Accordingly a supply of fluid medication is discharged through the fluid metering orifices to be collected in the fluid delivery chamber of the valve.

In operation, the patient holds the mouthpiece of the nebuliser in his mouth and inhales a supply of non-medicated ambient air. The ambient air supply travels distally along the air flow path of the nebulizer housing, whereby to impact and rotate the trigger ring. The trigger ring is rotated towards and into physical contact with the electrical contacts whereby to close the contacts and complete an electrical current path to a drive (e.g. battery) circuit. Accordingly, an electrical current path is established from the drive circuit to the piezoelectric disk by way of an upper and a lower holding post and the electrically conductive emitter plate. By virtue of the foregoing, the emitter plate and the emitter mesh coupled thereto are vibrated in harmony so as to accelerate the fluid medication collected in the delivery chamber of the fluid delivery valve. The fluid medication is pulled through the emitter mesh and reduced to a nebulized medication plume consisting of a fine mist of droplets. At the same time, the electrically conductive needle cannula support (i.e. antenna) is also energized by the drive circuit for generating electromagic energy to direct the nebulized medication plume through the emitter mesh and into the mouthpiece. The nebulized medication plume is mixed in the mouthpiece with the non-medicated ambient air supply inhaled by the patient and drawn through the air flow path of the housing to produce a medicated composite air stream that may be efficiently and reliably delivered to the respiratory tract of the patient through the deep lung.

DETAILED DESCRIPTION

Figure 1:
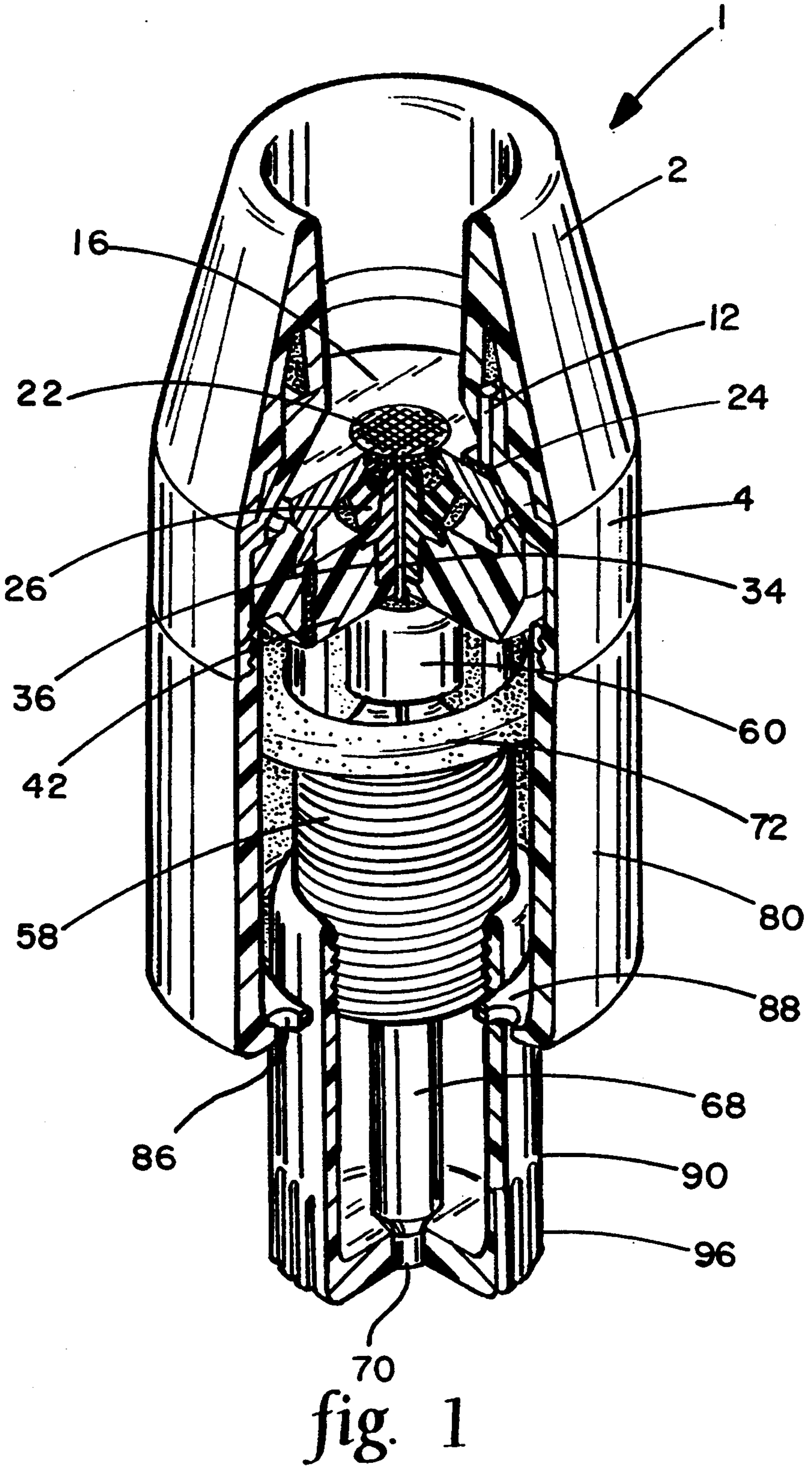
FIG. 1 is a perspective view, in partial cross-section, of the nebulizer which forms the present invention.
Figure 2:
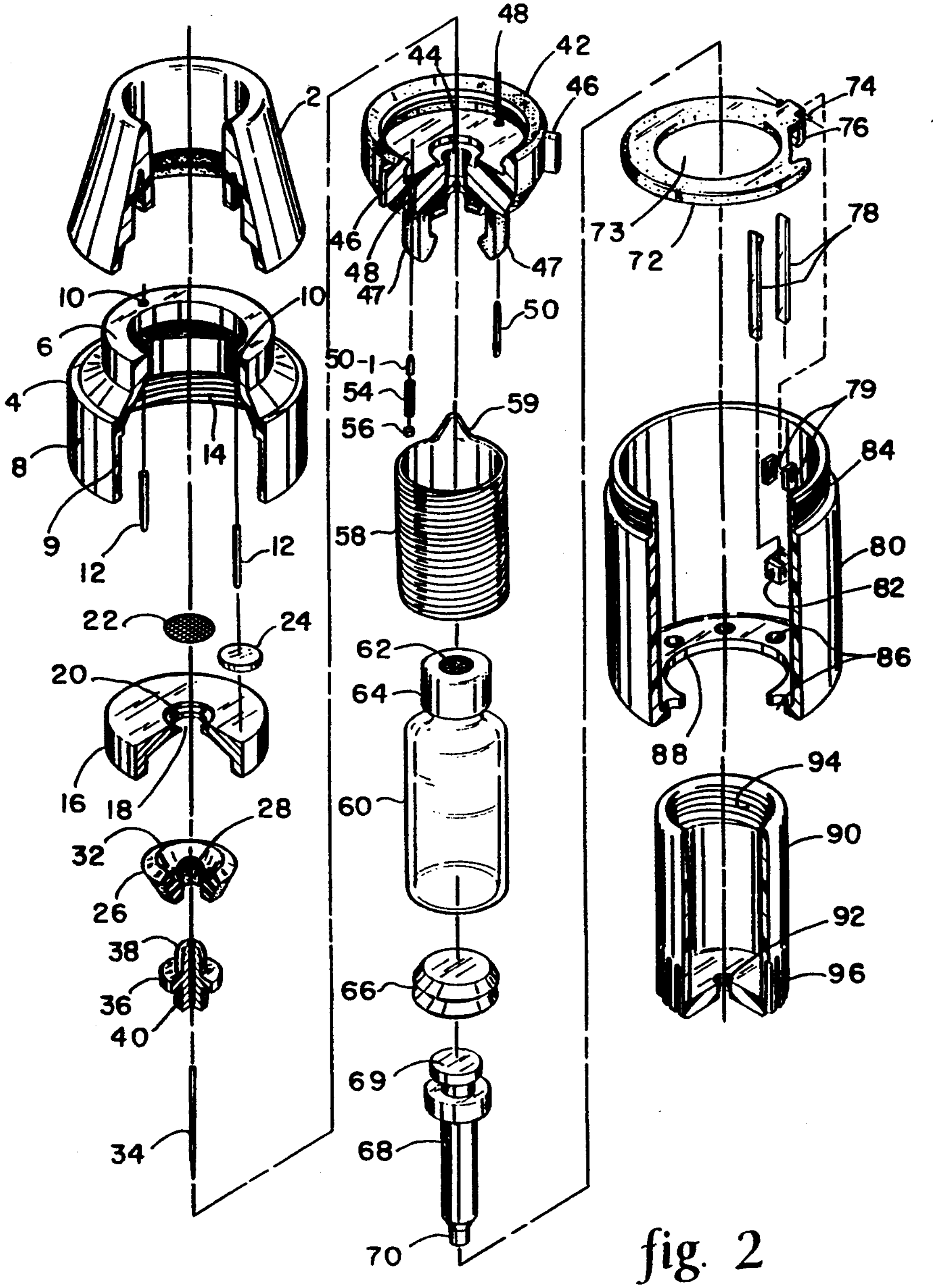
FIG. 2 is an exploded view of the nebulizer of FIG. 1.
Figure 3:
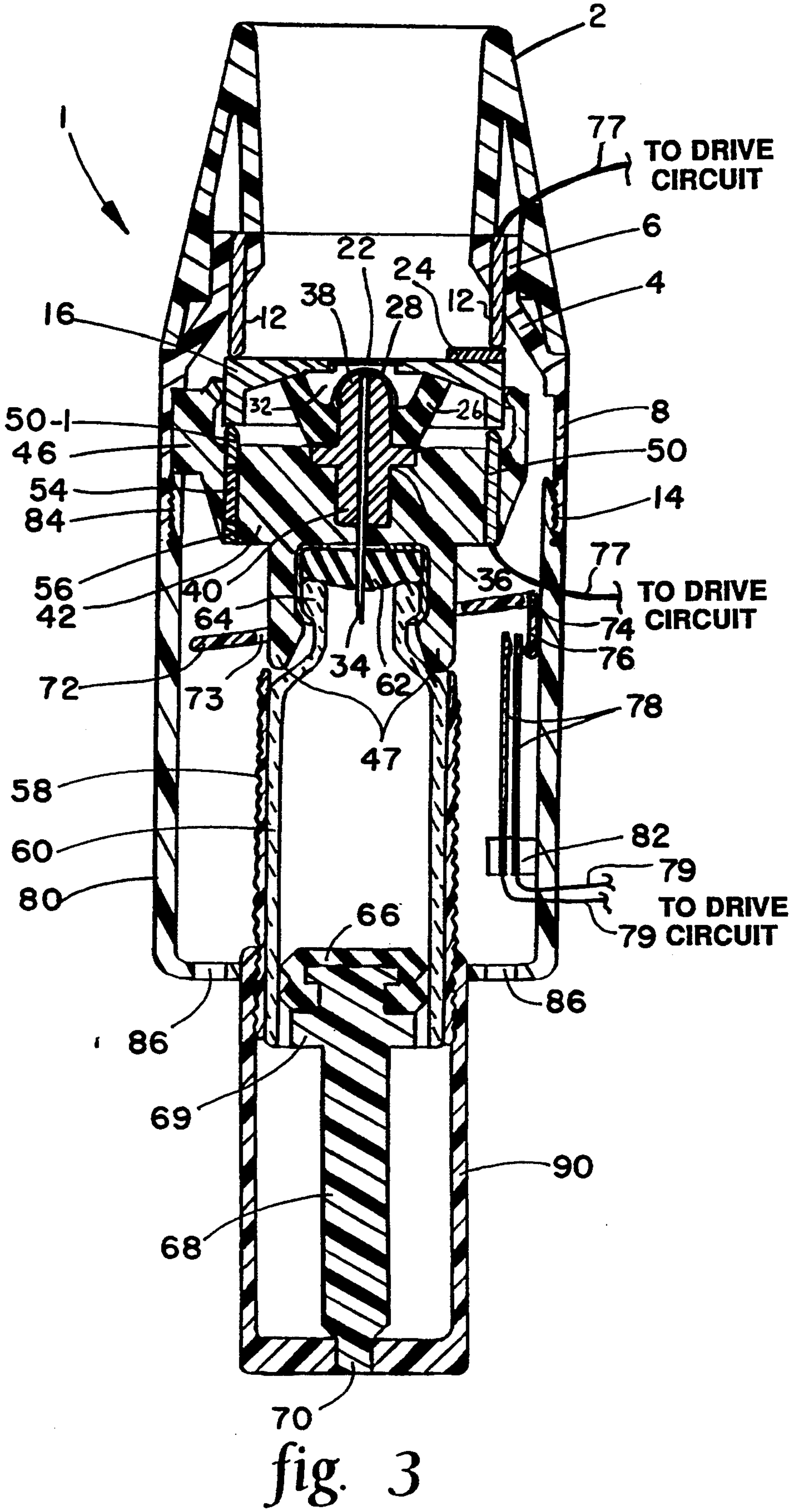
FIG. 3 is a cross-section of the nebulizer of FIG. 1.

The hand-held inhalation responsive nebuliser 1 which forms the present invention is now described in detail while referring initially to FIGS. 1–3 of the drawings. The nebuliser 1 includes a hollow, conically shaped replaceable/disposable mouthpiece 2 positioned at the distal end thereof. Located below the mouthpiece 2 is a hollow emitter base 4 having an upper support ring 6 and a lower cylindrical body 8. The diameter of the lower body 8 of emitter base 4 is larger than the diameter of the upper support ring 6 so that the hollow mouthpiece 2 can be removably and frictionally attached to emitter base 4 with the support ring 6 being received within and engaged by the mouthpiece 2. A pair of mounting holes 10 are formed longitudinally through the support ring 6 of emitter base 4 to receive respective electrically conductive upper holding posts 12 therethrough. A series of internal screw threads 14 extends around the periphery of the lower body 8, the function of which will be described hereinafter.

The upper holding posts 12 are received in mounting holes 10 and project proximally from the upper support ring 6 of emitter base 4 to both support and provide an electrical current path to an electrically conductive emitter plate 16 at the interior of the lower body 8 of emitter base 4. The emitter plate 16 has a central opening 18 formed therethrough with a peripheral seat 20 extending around the opening 18. Disposed within the seat 20 above the central opening 18 of emitter plate 16 is an emitter mesh 22. The emitter mesh 22 is a fine, screen-like matrix having apertures therein of approximately 3 to 5 microns. Bonded to the top of emitter plate 16 at one side of emitter mesh 22 is a piezoelectric disk 24.

Located proximally of the emitter plate 16 in spaced, axial alignment with the emitter mesh 22 is a unique, normally closed fluid delivery valve 26. The operation of fluid delivery valve 26 is important to the nebuliser 1 and will be described in greater detail when referring to FIGS. 4 and 5. Briefly, however, fluid delivery valve 26 includes a cup-like outer wall that surrounds a hemispherical membrane 28 having a plurality of fluid metering orifices (designated 30 and best shown in FIG. 4) formed therethrough. In the assembled nebuliser configuration (best shown in FIGS. 1 and 3), the fluid delivery valve 26 is retained beneath the emitter plate 16 with the hemispherical membrane 28 spaced immediately adjacent the emitter mesh 22. The area of fluid delivery valve 26 between the cup-like outer wall thereof and the inner hemispherical membrane 28 forms a fluid medication delivery chamber 32 in which fluid medication to be metered through the orifice 30 of membrane 28 is collected in order to be subsequently accelerated and pulled through the emitter mesh 22 that is seated upon the emitter plate 16.

A needle cannula 34 is held in coaxial alignment with the hemispherical membrane 28 of fluid delivery valve 26 and the emitter mesh 22 supported by emitter plate 16 by means of an electrically conductive cannula support 36 which, as will soon be described, also functions as an antenna to emit an electromagnetic energy field in the direction of the mesh 22. The cannula support 36 has a hemispherical head 38 which is received within and preserves the corresponding hemispherical shape of the membrane 28 of fluid delivery valve 26. With the nebulizer at rest, surface tension will hold the membrane 28 of valve 26 against the head 38 of cannula support 36 so as to prevent the flow of fluid through the fluid metering orifices 30 of membrane 28 and thereby maintain the normally closed condition of fluid delivery valve 26 (best shown in FIG. 4).

The distal end of the needle cannula 34 is retained by the head 38 of cannula support 36 so as to be surrounded by the hemispherical membrane 28 of fluid delivery valve 26. As will be described when referring to FIG. 5, a patient can operate the nebuliser 1 to cause a supply of fluid to be expulsed, under pressure, from the distal end of cannula 34, whereby to open the normally closed fluid valve 26 and thereby fill the fluid delivery chamber 32 of valve 26 with medicated fluid from a source of medication (e.g. a conventional pre-filled medication cartridge 60 in which a liquid pharmaceutical is stored). In this regard, and as is best shown in FIG. 3, the proximal end of cannula 34 projects outwardly from a cylindrical leg 40 of the cannula support 36 to penetrate the septum 62 of medication cartridge 60, whereby cannula 34 and cartridge 60 will lie in fluid communication with one another.

The cannula support 36 is retained in axial alignment with the emitter mesh 22 seated on emitter plate 16 by an emitter housing 42. The emitter housing 42 has a hole 44 extending longitudinally therethrough in which to receive the leg 40 of cannula support 36. The emitter housing 42 is attached to the emitter base 4 of nebuliser 1 by means of a pair of struts 46 which project radially from housing 42 for receipt within respective slots 9 formed in the lower body 8 of emitter base 4. Projecting proximally from the emitter housing 42 are a plurality of (e.g. four) gripping fingers 47 by which to surround and grasp the head 64 of the medication cartridge 60, whereby to couple the cartridge to the emitter housing 42 and thereby assure that the needle cannula 34 will remain in fluid communication with cartridge 60 through the septum 62 thereof.

A pair of mounting holes 48 extend longitudinally through the emitter housing 42 to receive therethrough respective electrically conductive lower holding posts 50. One of the holding posts 50-1 is spring-loaded and interfaced with an alignment contact spring 54 and a retaining plug 56. The lower holding posts 50 extend through mounting holes 48 and project distally from the emitter housing 42 in axial alignment with respective ones of the pair of upper holding posts 12 which project proximally from the emitter base 4. The pairs of upper and lower holding posts 12 and 50 permit vibration of the emitter plate 16 being supported therebetween, whereby the emitter mesh 22 carried by emitter plate 16 will be similarly vibrated to produce a nebuliser effect. The alignment contact spring 54, which is held in place by retaining plug 56, permits the holding post 50-1 to absorb mechanical shock and enables the upper and lower holding posts 12 and 50 to apply a constant pressure to and remain in electrical contact with the emitter plate 16.

A cylindrical sleeve 58 surrounds and is bonded to the medication cartridge 60. The exterior of sleeve 58 is threaded so as to be mated to a correspondingly threaded and rotatable dose control knob 90. Projecting distally from the threaded sleeve 58 is an alignment tab or key 59 which is dimensioned so as to be received within a keyway (not shown) formed in the emitter housing 42 and thereby prevent the rotation of sleeve 58 and the cartridge 60 bonded thereto when the dose selection control knob 90 is rotated by the patient.

Located at the proximal end of the medication cartridge 60 is a piston 66. The piston 66 is carried by the head 69 of an elongated piston stem 68. Disposed opposite the head 69 of piston stem 68 is a locator pin 70 that is sized to fit within a catch 92 of the rotatable dose selection control knob 90. In this manner, the piston stem 68 is affixed to the dose selection control knob 90 so that a rotation of knob 90 by the patient causes a corresponding distal relocation of the piston 66 through the cartridge 60 to expulse fluid medication through the needle cannula 34 and the orifices 30 of the hemispherical membrane 28 of the fluid delivery valve 26 to be collected in the fluid delivery chamber 32 thereof.

As another important feature of the present invention, an annular trigger ring 72 is provided to control the electrical energization of nubuliser 1 and the generation of a nebulised medication plume within the mouthpiece 2. In the assembled configuration of FIGS. 1 and 3, the trigger ring 72 surrounds the proximally extending fingers 47 of emitter housing 42 that grasp the head 64 of medication cartridge 60. Coextensively connected to the trigger ring 72 is a pivot pin 74. The pivot pin 74 is sized to be received between and rotatable within a pair of spaced, parallel aligned pivot supports 79 of a hollow, cylindrical top housing 80. With the pivot pin 74 in place, the trigger ring 72 extends laterally across the top housing 80 so as to lie within the air flow path of the nebuliser 1. The trigger ring 72 has a central opening 73 characterized by a sufficiently large diameter to receive the fingers 47 of the emitter housing 42 and to allow air flow therethrough.

Depending downwardly from the trigger ring 72 below the pivot pin 74 is a contact arm 76. The contact arm 76 is adapted to close a normally open electrical switch which consists of pair of flexible contact strips 78 that are spaced from one another and have a spring-like memory. First ends of the contact strips 78 are secured to a contact support block 82 at the interior of the top housing 80 so that the contacts 78 project longitudinally through the interior of housing 80 to lie adjacent the contact arm 76 of trigger ring 72.

As is best shown in FIG. 3, with the nebuliser 1 at rest, the trigger ring 72 is canted or angled slightly across the top housing 80 in a lateral direction so as to lie in generally perpendicular alignment with the air flow path therethrough such that the electrical contacts 78 are open. However, and as will be described in greater detail when referring to FIGS. 6 and 7, the trigger ring 72 is adapted to rotate at pivot pin 74 to correspondingly rotate the contact arm 76 thereof towards the normally open contacts 78 and thereby move the contacts together to complete an electrical current path to a drive circuit (not shown) which includes a conventional (e.g. lithium) battery that enables a nebulised air plume to be created within the mouthpiece 2 for inhalation by the patient.

A series of external screw threads 84 extends around the distal end of the cylindrical top housing 80. In the assembled configuration of FIGS. 1 and 3, the external screw threads 84 of top housing 80 are mated to the internal screw threads 14 of the emitter base 4, whereby to couple the top housing 80 and the emitter base 4 together. A series of evenly spaced air inlet holes 86 are formed through a support ring 88 at the proximal end of top housing 80 through which the dose selection control knob 90 is received and axially advanced.

As previously described, the dose selection control knob 90 includes a catch 92 at the proximal end thereof in which to receive the locator pin 70 of the piston stem 68. A series of internal screw threads 94 extends around the distal end of dose selection control knob 90. In the assembled configuration of FIGS. 1 and 3, the screw threads 94 of dose selection control knob 90 are mated to the external screw threads of the sleeve 58 which surrounds and is bonded to the fluid medication cartridge 60. Thus, and as will soon be disclosed, a rotation of the dose selection control knob 90 causes the control knob 90 to ride around the external screw threads of and move axially relative to the sleeve 58. To this end, a knurled gripping surface 96 is formed around the proximal end of dose selection control knob 90 to facilitate the rotation of knob 90 by the patient.

Accordingly, the dose selection control knob 90 will be simultaneously rotated around the threaded sleeve 58 and advanced axially through the top housing 80 via the proximal support ring 88 thereof. Being that the locator pin 70 of piston stem 68 is captured by the catch 92 of dose selection control knob 90, an axial displacement of dose selection control knob 90 will cause a corresponding axial displacement of the piston 66 through the medication cartridge 60 so as to expulse fluid medication through the needle cannula 34. In this regard, it should be observed that the alignment key 59 of threaded sleeve 58 engages the emitter housing 42 and prevents a rotation of sleeve 58 at the same time that the dose selection control knob 90 is rotated around sleeve 58 and moved axially therealong.

The operation of the nebuliser 1 of the present invention is now described while referring concurrently to FIGS. 4–7 of the drawings. Initially, the patient rotates the dose selection control knob 90 around the threaded sleeve 58. As previously disclosed, the control knob 90 is both rotated and moved axially (i.e. distally) through the top housing 80, whereby to cause a corresponding axial displacement of the piston stem 68 which is attached to the dose selection control knob 90 by the receipt of locator pin 70 in catch 92. Accordingly, the piston 66 is advanced through the fluid medication cartridge 60 to force a medicated fluid into the proximal end of the needle cannula 34. As should now be apparent, the patient can selectively control the volume of fluid forced from cartridge 60 into cannula 34 depending upon the number of revolutions made by the dose selection control knob 90.

Figure 4:
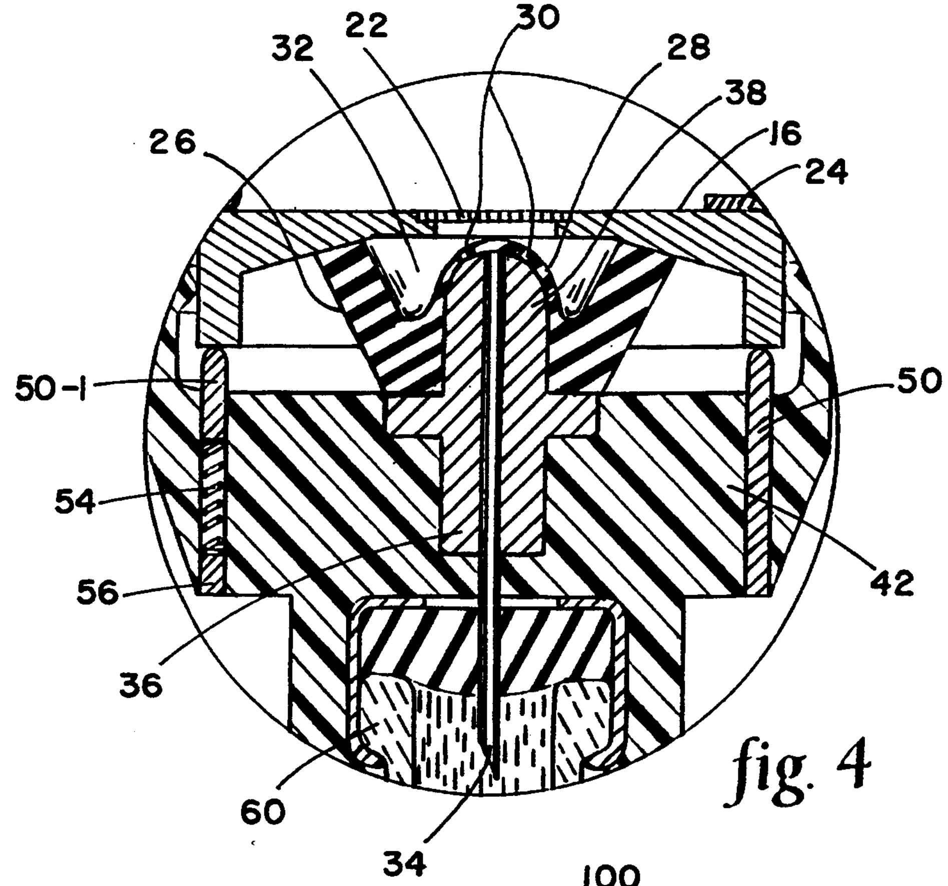
FIG. 4 is an enlarged detail in cross-section showing the fluid delivery valve of the nebulizer in its normally closed condition.

FIG. 4 of the drawings shows the nebuliser 1 at rest and prior to the rotation of the dose selection control knob 90 by the patient. In this case, there is no fluid within the cannula 34, and the fluid delivery valve 26 is closed. That is to say, the hemispherical membrane 28 of valve 26 is received flush against the hemispherical head 38 of the cannula support 36 so that the fluid metering orifices 30 through membrane 28 are closed to the passage of fluid.

Figure 5:
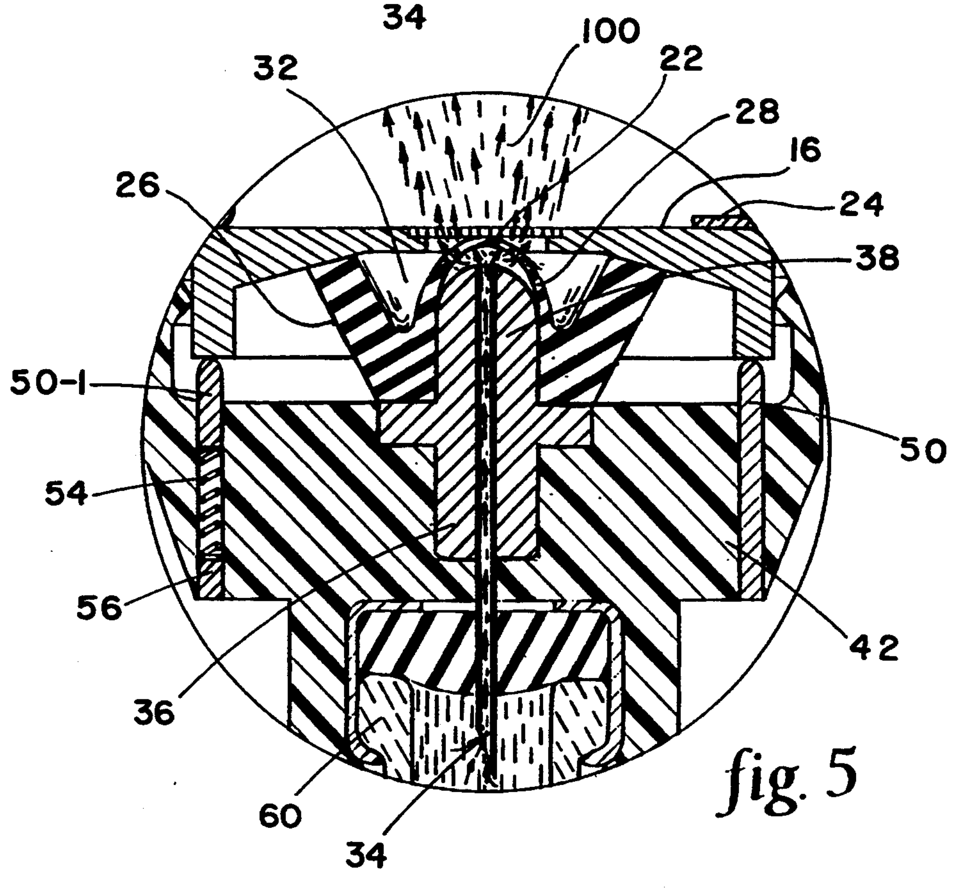
FIG. 5 is an enlarged detail in cross-section showing the fluid delivery value in the open condition so that a nebulized medication plume is generated.

When the patient rotates the dose selection control knob 90, fluid from the medication cartridge 60 will be expulsed from the distal end of the needle cannula 34 to distend the hemispherical membrane 28 of fluid delivery valve 26. More particularly, and as is best shown in FIG. 5 of the drawings, the pressure of the fluid medication being expulsed from the cannula 34 urges the membrane 28 and the fluid metering orifices 30 thereof away from the hemispherical head 38 of cannula support 36. Hence, the fluid metering orifices 30 are no longer closed to the passage of fluid expulsed from cannula 34, such that fluid delivery valve 26 is now open and a supply of fluid from cartridge 60 can be collected in the fluid delivery chamber 32 of valve 26.

Figure 6:
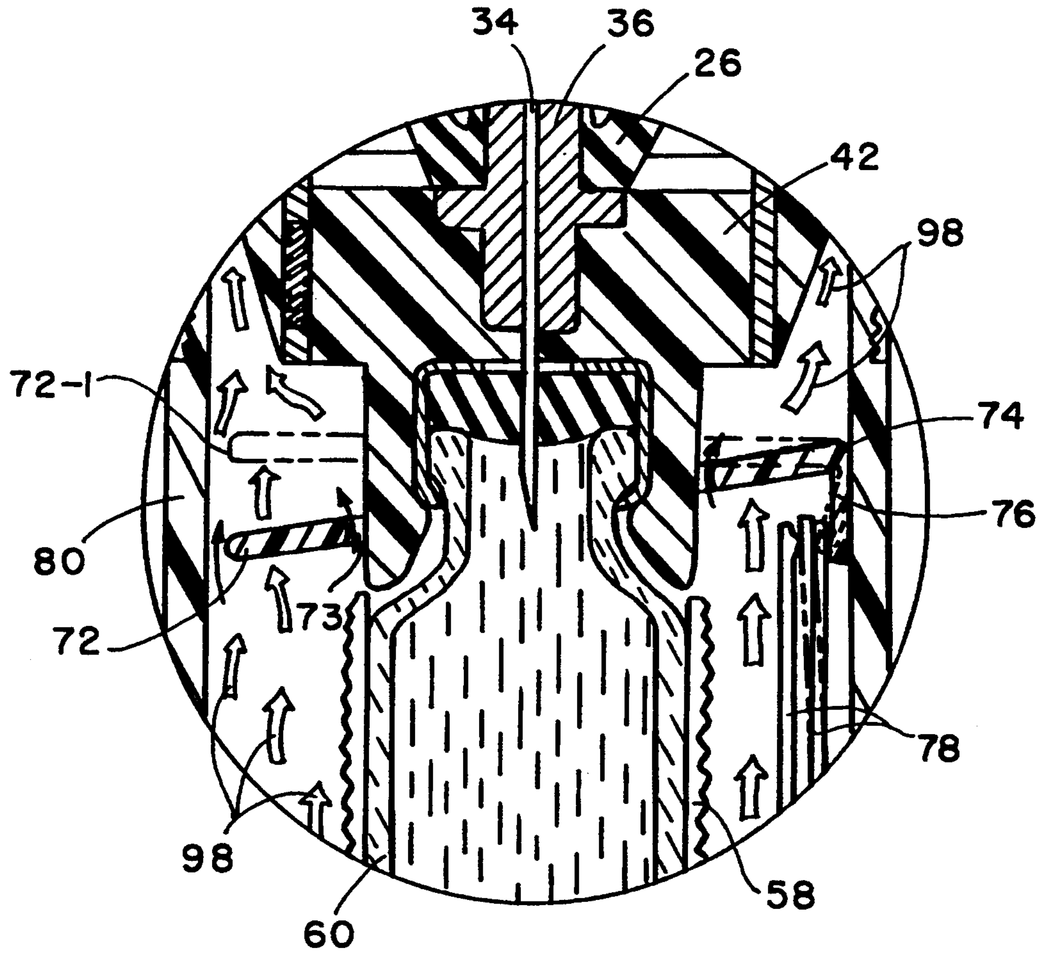
FIG. 6 is an enlarged detail in cross-section showing the distal flow path of the non-medicated ambient air supply being drawn through the housing of the nebulizer.

At this point, the patient holds the nebuliser 1 with the mouthpiece 2 located in his mouth. The patient then inhales to draw a stream 98 of fresh, non-medicated ambient air into the top housing 80 via the air inlet holes 86 thereof (best shown in FIG. 7). The stream 98 of non-medicated ambient air moves distally through the top housing 80 towards the trigger ring 72. As is best shown in FIG. 6, the impact of the ambient air stream 98 striking the trigger ring 72 within the air flow path of top housing 80 causes the ring 72 to rotate distally at the pivot pin 74 thereof from a slightly canted orientation to a fully horizontal orientation (shown in phantom lines and represented by the reference numeral 72-1) extending laterally across housing 80. The distal rotation of trigger ring 72 causes a corresponding rotation of the contact arm 76 towards and into contact with the pair of spaced, electrical contacts 78.

The rotation of contact arm 76 in response to the rotation of trigger ring 72 generates an impact force to close the contacts 78 against one another and thereby complete an electrical current path to the aforementioned drive circuit via a pair of electrical wires 79. Accordingly, the drive circuit is now connected to supply current to and energize one of each pair of the axially aligned upper and lower holding posts 12 and 50 via a pair of electrical wires 77 (best shown in FIG. 7). Moreover, the cannula support (i.e. antenna) 36 is also connected to the drive circuit to be energized thereby via an additional wire (not shown).

When the contacts 78 are closed by the rotation of contact arm 76 of trigger ring 72 in response to the inhalation of the patient and the resulting distally moving stream 98 of non-medicated air through top housing 80, electrical energy will be supplied from the drive circuit to the piezoelectric disk 24 by way of the electrically conductive holding posts 12 and 50 and the electrically conductive emitter plate 16 coupled thereto. Hence, the piezoelectric disk 24 mounted on the emitter plate 16 will begin to vibrate. The vibration of piezoelectric disk 24 is transferred through the emitter plate 16 to the emitter mesh 22 seated on emitter plate 16 above the needle cannula 34 and the fluid delivery chamber 32 of the fluid delivery valve 26.

Figure 7:
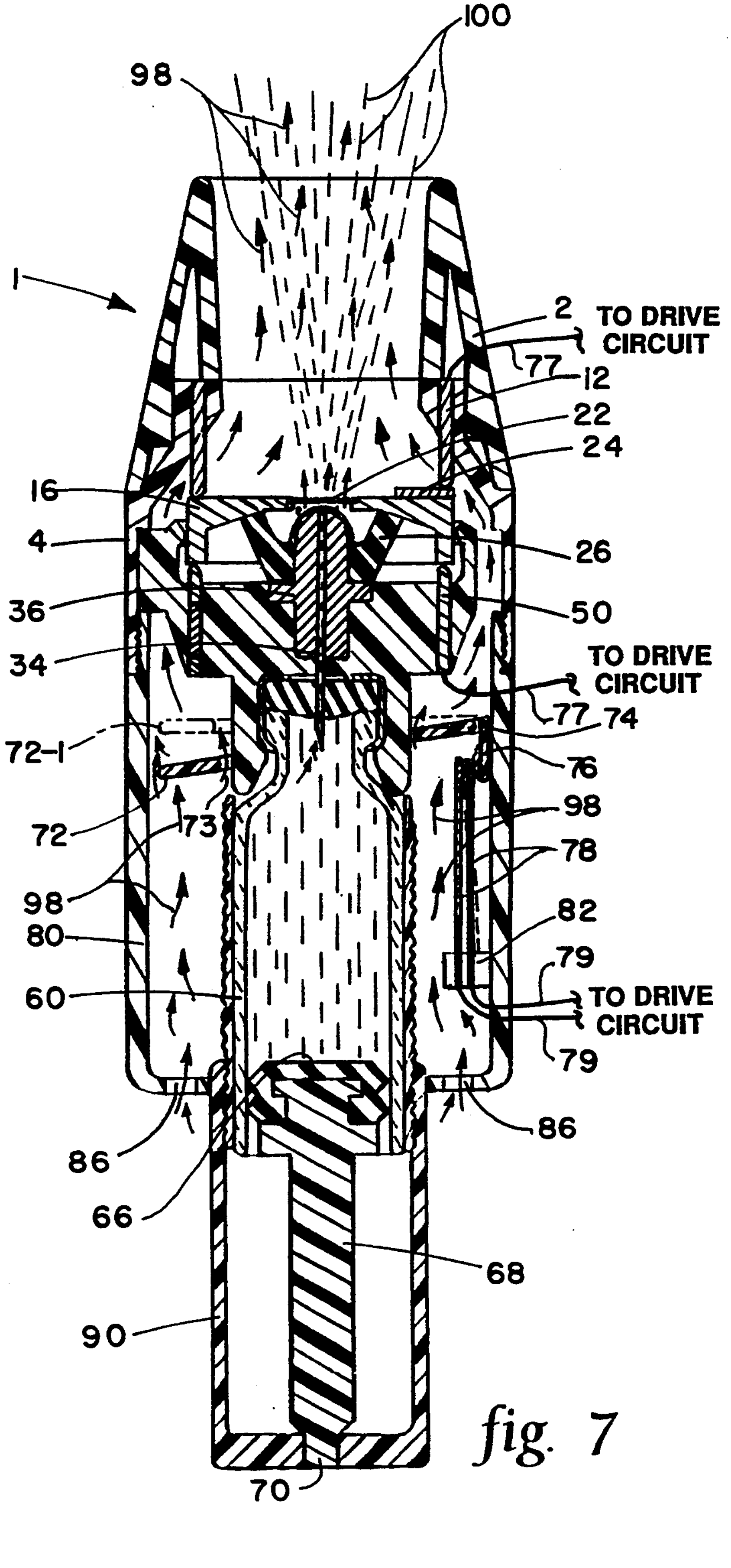
FIG. 7 shows the nebulized medication plume mixed with the non-medicated ambient air supply at the mouthpiece of the nebulizer to produce a composite air stream to be inhaled by the patient to the deep lung.

Accordingly, the emitter mesh 22 will vibrate at a high frequency and in harmony with the piezoelectric disk 24, such that fluid from the medication cartridge 60 that has been expulsed from the cannula 34 and collected in the fluid delivery chamber 32 will be accelerated and pulled through the emitter mesh 22 so as to be reduced thereby into a fine mist of droplets (i.e. a nebulised medication plume designated 100 and best illustrated in FIGS. 5 and 7). At the same time, the electrically conductive cannula support (i.e. antenna) 36 is also energized by the drive circuit to generate electromagnetic energy which directs the nebulised plume 100 through the mesh 22 and into the mouthpiece 2.

Referring particularly now to FIG. 7 of the drawings, an inner, central nebulised medication plume 100 being pulled through the emitter mesh 22 is shown mixed in the mouthpiece 2 of nebuliser 1 with an outer, tubular non-medicated air stream 98 inhaled distally through the top housing 80 via air inlet holes 86 and moved through the central opening 73 of and around the trigger ring 72. The resultant composite air stream formed within the mouthpiece 2, consisting of a metered amount of fluid medication from cartridge 60 and non-medicated ambient air, will effectively and reliably enter the respiratory system of the patient to provide relief depending upon the contents of cartridge 60.

At the conclusion of each inhalation, the spring-like memory of the flexible contacts 78 will push the contact arm 76 of trigger ring 72 away from such contacts. Therefore, the trigger ring 72 will rotate proximally at pivot pin 74 thereof to return to its canted, at rest position across the top housing 80 to await the next breath of the patient. What is more, the electrical contacts 78 will separate to open the electrical circuit path to the drive circuit. With the circuit path open, the piezoelectric disk 24 and the antenna 36 will be de-energized, and the formerly vibrating emitter mesh 22 will become stationary. Thus, fluid will no longer be pulled through the mesh 22 and the nebulised effect (which is synchronized with the patient's inhalation through mouthpiece 2) will terminate.

It will be apparent that while a preferred embodiment of the invention has been shown and described, various modifications and changes may be made without departing from the true spirit and scope of the invention.

Having thus set forth the preferred embodiment, what is claimed is:

1. An inhalation responsive nebuliser surrounded by ambient air and comprising:

a hollow housing having proximal and distal ends and an air flow path extending therebetween;

a mouthpiece attached to the distal end of said housing at which a patient's inhalation draws a supply of the ambient air distally through the air flow path of said housing and into said mouthpiece;

an emitter mesh located within said housing and communicating with said mouthpiece;

cartridge means in which to store a fluid medication, said cartridge means including a piston located at one end thereof;

means to deliver a supply of said fluid medication from said cartridge means to said emitter mesh; and electric drive circuit means including electrical switch means, said electrical switch means responsive to the supply of ambient air drawn through the air flow path of said housing for connecting said drive circuit means to said emitter mesh and causing said emitter mesh to vibrate, whereby the fluid medication delivered to said emitter mesh from said cartridge means passes through said mesh as a mist to be mixed with the supply of ambient air in said mouthpiece.

2. The nebuliser recited in claim 1, in which said electrical switch means includes a pair of normally open electrical contacts and ambient air responsive means extending laterally across said housing in substantially perpendicular alignment with the air flow path thereof, the supply of ambient air drawn distally though said air flow path of said housing displacing said ambient air responsive means so as to close said pair of electrical contacts and connect said electrical drive circuit means to said emitter mesh.

3. The nebuliser recited in claim 2, wherein said ambient air responsive means extending laterally across said housing in substantially perpendicular alignment with said air flow path thereof is a trigger ring surrounding said cartridge means.

4. The nebuliser recited in claim 3, wherein said trigger ring is pivotally connected to said housing, the supply of ambient air drawn distally through said air flow path rotating said trigger ring into physical contact with said pair of electrical contacts to close said contacts and connect said electrical drive circuit to said emitter mesh.

5. The nebuliser recited in claim 1, wherein said electrical drive circuit means also includes an electrically conductive emitter plate having an opening therethrough, said emitter mesh seated on said emitter plate to cover said opening.

6. The nebuliser recited in claim 5, wherein said electrical drive circuit means also includes a piezoelectric disk attached to said emitter plate, said electrical drive circuit means causing said piezoelectric disk to vibrate, which vibration is transferred to said emitter mesh by way of said emitter plate.

7. The nebuliser recited in claim 6, wherein said electrical drive circuit means also includes upper and lower electrically conductive holding posts for applying pressure to and retaining said emitter plate for vibration therebetween.

8. The nebuliser recited in claim 1, wherein said means to deliver a supply of fluid from said cartridge means to said emitter mesh is a needle cannula located in fluid communication with said cartridge means, said nebuliser further comprising fluid deliver valve means positioned between said needle cannula and said emitter mesh to control the delivery of said supply of fluid to said emitter mesh.

9. The nebuliser recited in claim 8, further comprising a dose selection control knob located at the proximal end of said housing and movable distally therethrough, said dose selection control knob connected to said piston, such that a distal movement of said control knob causes a corresponding axial movement of said piston through said medication cartridge for forcing fluid medication into said needle cannula to be expulsed therefrom.

10. The nebuliser recited in claim 8, wherein said fluid delivery valve means includes a flexible membrane having at least one fluid orifice formed therethrough and closed to the passage of said fluid medication, said flexible membrane being distended towards said emitter mesh in response to said fluid medication being expulsed from said needle cannula to open said fluid orifice and enable said supply of fluid medication to be delivered to said emitter mesh.

11. The nebuliser recited in claim 10, further comprising an electrically conductive needle cannula support located in said housing for retaining said needle cannula between said cartridge means and the flexible membrane of said fluid delivery valve means, said membrane seated upon said needle cannula support so that said at least one fluid orifice of said membrane is closed against said support.

12. A nebuliser comprising:

a hollow housing having proximal and distal ends and an air flow path extending therebetween;

a mouthpiece attached to the distal end of said housing at which a patient's inhalation draws air distally through the air flow path of said housing and into said mouthpiece;

an emitter mesh located within said housing and communicating with said mouthpiece;

cartridge means in which to store a fluid medication; and means to deliver a supply of said fluid medication from said cartridge means to said emitter mesh including fluid valve means located between said emitter mesh and said cartridge means, said fluid valve means having a flexible membrane with at least one fluid orifice formed therethrough that is closed to the delivery of said supply of said fluid medication from said cartridge means to said emitter mesh, said flexible membrane being distended towards said emitter mesh in response to said supply of said fluid medication from said cartridge means to thereby open said fluid orifice to the delivery of said supply of fluid medication from said cartridge means to said emitter mesh.

13. The nebuliser recited in claim 12, further comprising electrical drive circuit means including electrical switch means, said electrical switch means responsive to the supply of air drawn through the air flow path of said housing for connecting said drive circuit means to said emitter mesh and causing said emitter mesh to vibrate, whereby the fluid medication delivered to said emitter mesh from said cartridge means passes through said mesh as a mist to be mixed with the supply of air in said mouthpiece.

14. The nebuliser recited in claim 13, wherein said electrical switch means includes a pair of normally open electrical contacts and air responsive means extending laterally across said housing in substantially perpendicular alignment with the air flow path thereof, the supply of air drawn distally though the air flow path of said housing displacing said air responsive means so as to close said pair of electrical contacts and connect said electrical drive circuit means to said emitter mesh.

15. The nebuliser recited in claim 14, wherein said air responsive means extending laterally across said housing in substantially perpendicular alignment with said air flow path thereof is a trigger ring surrounding said cartridge means.

16. The nebuliser recited in claim 15, wherein said trigger ring is pivotally connected to said housing, the supply of air drawn distally through said air flow path rotating said trigger ring into physical contact with said pair of electrical contacts to close said contacts and connect said electrical drive circuit means to said emitter mesh.

17. The nebuliser recited in claim 13, wherein said electrical drive circuit means also includes an electrically conductive emitter plate having an opening therethrough and a piezoelectric disk attached to said emitter plate, said emitter mesh seated on said emitter plate to cover said opening, and said electrical drive circuit means causing said piezoelectric disk to vibrate, which vibration is transferred to said emitter mesh by way of said emitter plate.

18. The nebuliser recited in claim 12, wherein said means to deliver a supply of fluid from said cartridge means to said emitter mesh also includes a needle cannula located in fluid communication with said cartridge means, the flexible membrane of said fluid valve means positioned between said needle cannula and said emitter mesh to control the delivery of said supply of fluid to said emitter mesh via said needle cannula.

19. The nebuliser recited in claim 18, further comprising a piston moving axially through said cartridge means and a dose selection control knob located at the proximal end of said housing and moving distally therethrough, said dose selection control knob connected to said piston such that a distal movement of said control knob causes a corresponding axial movement of said piston through said cartridge means for forcing fluid medication into said needle cannula from said cartridge means.

20. The nebuliser recited in claim 18, further comprising an electrically conductive needle cannula support located in said housing for retaining said needle cannula between said cartridge means and the flexible membrane of said fluid valve means, said membrane seated upon said needle cannula support so that said at least one fluid orifice of said membrane is closed against said support.

* * * * *